United States Patent [19]

Holderbaum et al.

[11] Patent Number: 5,266,320
[45] Date of Patent: Nov. 30, 1993

[54] AMINOVINYL-SUBSTITUTED HETEROCYCLIC COMPOUNDS AS STABILIZERS FOR ORGANIC MATERIALS

[75] Inventors: Martin Holderbaum, Ludwigshafen; Alexander Aumueller, Neustadt; Hubert Trauth, Dudenhofen, all of Fed. Rep. of Germany

[73] Assignee: BASF Aktiengesellschaft, Ludwigshafen, Fed. Rep. of Germany

[21] Appl. No.: 835,483

[22] Filed: Feb. 14, 1992

[30] Foreign Application Priority Data

Mar. 8, 1991 [DE] Fed. Rep. of Germany ....... 4107379

[51] Int. Cl.$^5$ .................. A61K 7/42; A61K 7/027
[52] U.S. Cl. ..................... 424/401; 424/45;
424/59; 424/78.03; 424/475; 424/476; 514/367;
514/375; 514/394; 514/944; 514/945; 514/972;
252/401; 252/402; 252/403; 524/93; 524/94;
548/152; 548/178; 548/179; 548/180; 548/217;
548/309.7
[58] Field of Search .............. 424/401, 45, 59, 78.03,
424/475, 476; 514/366, 367, 375, 394, 395, 944,
945, 972; 524/93, 94; 252/401, 402, 403

[56] References Cited

U.S. PATENT DOCUMENTS 3,079,366 2/1963 Boyle et al. ................... 260/459

FOREIGN PATENT DOCUMENTS 984013 2/1965 United Kingdom .

OTHER PUBLICATIONS

CA 109(26): 240609t.
Journal of Heterocyclic Chemistry, vol. 23, Sep.-Oct. 1986, pp. 1443-1449, K. Takagi, et al., "Synthesis of Pyrimidino[4,5-b][1,5]Benzodiazepin-2-Ones And Pyrimidino[1,6-a]Benzimidazol-1-Ones From 4-Ethoxycarbonylamino-1H-1,5-Benzodiazpine-3-Carbonitrile ... ".
Journal of Heterocyclic Chemistry, vol. 28, No. 2, Feb.-Mar. 1991, pp. 485-487, T. Aotsuka, et al., "Ring Transformation Of 4-Amino-1H-1,5-Benzodiazepine-3-Carbonitrile And Ethyl 4-Amino-1-H-1,5-Benzodiazepine-3-Carboxylate Into Benzimidazole ... ".

Primary Examiner—Thurman K. Page
Assistant Examiner—Jyothsna Venkat
Attorney, Agent, or Firm—Oblon, Spivak, McClelland, Maier & Neustadt

[57] ABSTRACT

The use of an aminovinyl-substituted heterocyclic compound of the general formula I

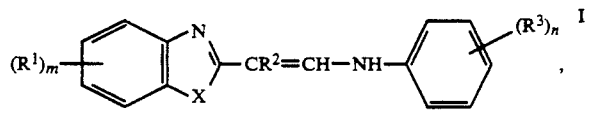

in which $R^1$ denotes hydrogen, $C_1$-$C_4$-alkyl, $C_1$-$C_4$-alkoxy, or halogen, and, if more than one radical $R^1$ are present, these may be the same or different, $R^2$ denotes cyano or $C_1$-$C_{20}$-alkoxycarbonyl or $C_3$-$C_6$-cycloalkoxycarbonyl, $R^3$ denotes hydrogen, $C_1$-$C_{18}$-alkyl, $C_1$-$C_{18}$-alkoxy, halogen, cyano, $C_1$-$C_{20}$-alkoxycarbonyl, or $C_3$-$C_6$-cycloalkoxycarbonyl, and, if more than one radical $R^3$ are present, these may be the same or different, X denotes NH, O or S, m is equal to 1 or 2, and n is an integer from 1 to 5, as a stabilizer for organic materials.

8 Claims, No Drawings

AMINOVINYL-SUBSTITUTED HETEROCYCLIC COMPOUNDS AS STABILIZERS FOR ORGANIC MATERIALS

The present invention relates to the use of an aminovinyl-substituted heterocyclic compound of the general formula I

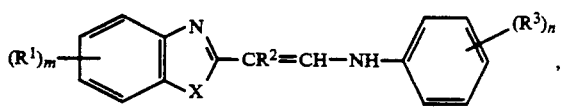

in which
- $R^1$ denotes hydrogen, $C_1$-$C_4$-alkyl, $C_1$-$C_4$-alkoxy, or halogen, and, if more than one radical $R^1$ are present, these may be the same or different,
- $R^2$ denotes cyano or $C_1$-$C_{20}$-alkoxycarbonyl or $C_3$-$C_6$-cycloalkoxycarbonyl,
- $R^3$ denotes hydrogen, $C_1$-$C_{18}$-alkyl, $C_1$-$C_{18}$-alkoxy, halogen, cyano, $C_1$-$C_{20}$-alkoxycarbonyl, or $C_3$-$C_6$-cycloalkoxycarbonyl, and, if more than one radical $R^3$ are present, these may be the same or different,
- X denotes NH, O or S,
- m is equal to 1 or 2, and
- n is an integer from 1 to 5, as a stabilizer for organic materials.

Some of the aminovinyl-substituted heterocyclic compounds represented by formula I are novel compounds.

The invention further relates to organic materials which contain said compounds I and are thus stabilized to the action of light, oxygen, and heat, especially stabilized plastics and paint formulations, and to cosmetic preparations containing said compounds I as light stabilizers.

It is well known that organic materials, particularly plastics and paints, degrade rapidly, especially under the action of light. Such degradation is usually noticeable from yellowing or other discoloration of the material, or from it becoming crazed or brittle. The prior art light stabilizers and other prior art stabilizers have not given satisfactory results as regards protection of organic materials from degradation due to the action of light, oxygen, and heat.

For example, U.S. Pat. No. 3,079,366 recommends the use of, inter alia, arylaminoethylenes of formula IV below

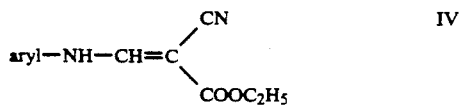

as uv absorbers for plastics. Although these compounds IV exhibit the desired spectroscopic properties, their stabilizing action fails to meet present-day requirements. In particular, plastics stabilized with compounds IV still show a pronounced tendency to discoloration.

It is thus an object of the invention to provide light stabilizers and other stabilizers which are capable of effectively stabilizing organic material in the desired manner.

Accordingly, we have found the above-defined method of using aminovinyl-substituted heterocyclic compounds I.

Apart from hydrogen, $R^1$ can be $C_1$-$C_4$-alkyl, e.g. methyl, ethyl, n-propyl, iropropyl, n-butyl, isobutyl, s-butyl, and t-butyl, $C_1$-$C_4$-alkoxy, e.g. methoxy, ethoxy, n-propoxy, isopropoxy, n-butoxy, isobutoxy, s-butoxy, and t-butoxy, and also halogen such as fluorine, chlorine, bromine, and iodine. Of these, hydrogen, methyl, methoxy, and chlorine are preferred, and hydrogen is most preferred. The radicals $R^1$ are preferentially in position 5 and/or 6 of the benzimidazole system.

The radical $R^2$ is cyano or, preferably, alkoxycarbonyl, the alkyl moiety of this alkyl carboxylate function being, in particular, $C_1$-$C_{20}$-alkyl, although it can alternatively be $C_3$-$C_6$-cycloalkyl. Examples of such a straight-chain or branched-chain $C_1$-$C_{20}$-alkyl moiety are, in particular, methyl, ethyl, n-propyl, isopropyl, n-butyl, isobutyl, s-butyl, t-butyl, n-pentyl, n-hexyl, n-heptyl, n-octyl, 2-ethylhexyl, n-nonyl, isononye, n-decyl, isodecyl, n-undecyl, n-dodecyl n-tridecyl, isotridecyl, n-tetradecyl, n-pentadecyl, n-hexadecyl, n-heptadecyl, n-octadecyl, and n-eicosyl. Of these, the long-chain alkyl radicals may be of synthetic origin, produced for example by oxo-synthesis or Ziegler-synthesis, or they may be derived from natural fatty alcohols. Examples of suitable $C_3$-$C_6$-cycloalkyl groups are cyclopropyl, cyclobutyl, cyclopentyl, and especially cyclohexyl.

The substituents $R^3$ on the phenyl nucleus may be hydrogen atoms or straight-chain or branched-chain $C_1$-$C_{18}$-alkyl groups, such as, in particular, $C_1$-$C_4$-alkyl groups, for example n-propyl, isopropyl, n-butyl, isobutyl, s-butyl, t-butyl, and most particularly methyl and ethyl, besides n-pentyl, n-hexyl, n-heptyl, n-octyl, 2-ethylhexyl, n-nonyl, isononyl, n-decyl, isodecyl, n-undecyl, n-dodecyl, n-tridecyl, isotridecyl, n-tetradecyl, n-pentadecyl, n-hexadecyl, n-heptadecyl, and n-octadecyl. Of these, the long-chain alkyl radi of synthetic origin, produced for example by oxo-synthesis or Ziegler-synthesis, or they may be derived from natural fatty alcohols.

The substituents $R^3$ may alternatively be straight-chain or branched-chain $C_1$-$C_{18}$-alkoxy groups, such as, in particular, $C_1$-$C_4$-alkoxy, for example n-propoxy, isopropoxy, n-butoxy, isobutoxy, s-butoxy, t-butoxy, and most particularly methoxy and ethoxy, besides n-pentoxy, n-hexoxy, n-heptoxy, n-octoxy, 2-ethylhexoxy, n-nonoxy, isononoxy, n-decyloxy, isodecyloxy, n-undecyloxy, n-dodecyloxy, n-tridecyloxy, isotridecyloxy, n-tetradecyloxy, n-pentadecyloxy, n-hexadecyloxy, n-heptadecyloxy, and n-octadecyloxy. Of these, the long-chain alkyl radicals may be of synthetic origin, produced for example by oxo-synthesis or Ziegler-synthesis, or they may be derived from natural fatty alcohols.

Other meanings of $R^3$ are halogen, e.g. fluorine, bromine, iodine, and especially chlorine; cyano; and alkoxycarbonyl in which the alkyl moiety of the alkyl carboxylate function is preferably a $C_1$-$C_{20}$-alkyl group, more preferably a $C_1$-$C_{12}$-alkyl group, and most preferably a $C_1$-$C_8$-alkyl group, but can alternatively be a $C_3$-$C_6$-cycloalkyl group. Examples of such $C_1$-$C_{20}$-alkyl groups and $C_3$-$C_6$-cycloalkyl groups are listed above in the description of the various meanings of $R^2$.

The number of substituents $R^3$ on the phenyl nucleus, designated by n, may be 1 to 5 and is preferably 1 or 2.

The variable X stands for O, S or, in particular, NH. In the latter case, the compound is a benzimidazole, whilst when X=O it is a benzoxazole and when X=S a benzthiazole.

The preferred stabilizers for organic materials are 2-(aminovinyl)benzimidazoles I (X=NH), in which
$R^1$ denotes hydrogen, methyl, methoxy, or chlorine,
$R^2$ denotes cyano or $C_1$-$C_{20}$-alkoxycarbonyl,
$R^3$ denotes hydrogen, $C_1$-$C_4$-alkyl, $C_1$-$C_4$-alkoxy, chlorine, cyano, or $C_1$-$C_{12}$-alkoxycarbonyl,
m is equal to 1 or 2, and
n is equal to 1 or 2.

Of these, particularly preferred 2-(aminovinyl)benzimidazoles I (X=NH) are those in which
$R^1$ denotes hydrogen,
$R^2$ denotes $C_1$-$C_{20}$-alkoxycarbonyl,
$R^3$ denotes hydrogen, methyl, ethyl, methoxy, ethoxy, chlorine, cyano, or $C_1$-$C_8$-alkoxycarbonyl, and
n is equal to 1 or 2.

Some of the aminovinyl-substituted heterocyclic compounds I are novel compounds. Thus the invention further relates to aminovinyl-substituted heterocyclic compounds of the general formula I

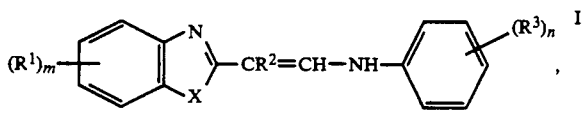

in which
$R^1$ denotes hydrogen, $C_1$-$C_4$-alkyl, $C_1$-$C_4$-alkoxy, or halogen, and, if more than one radical $R^1$ are present, these may be the same or different,
$R^2$ denotes cyano or $C_1$-$C_{20}$-alkoxycarbonyl or $C_3$-$C_6$-cycloalkoxycarbonyl,
$R^3$ denotes hydrogen, $C_1$-$C_{18}$-alkyl, $C_1$-$C_{18}$-alkoxy, halogen, cyano, $C_1$-$C_{20}$-alkoxycarbonyl, or $C_3$-$C_6$-cycloalkoxycarbonyl, and, if more than one radical $R^3$ are present, these may be the same or different,
X denotes NH, O or S,
m is equal to 1 or 2, and
n is an integer from 1 to 5,
with the exception of the compounds for which the meanings of the variables are as follows: $R^1$=hydrogen, $R^2$=cyano, $R^3$=hydrogen or p-methoxy, X=NH.

The invention particularly relates to aminovinyl-substituted heterocyclic compounds of the general formula I

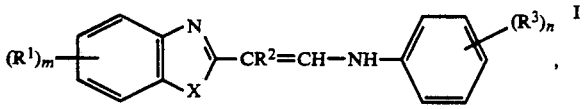

in which
$R^1$ denotes hydrogen, $C_1$-$C_4$-alkyl, $C_1$-$C_4$-alkoxy, or halogen, and, if more than one radical $R^1$ are present, those may be the same or different,
$R^2$ denotes cyano or $C_1$-$C_{20}$-alkoxycarbonyl or $C_3$-$C_6$-cycloalkoxycarbonyl,
$R^3$ denotes hydrogen, $C_1$-$C_{18}$-alkyl, $C_1$-$C_{18}$-alkoxy, halogen, cyano, $C_1$-$C_{20}$-alkoxycarbonyl, or $C_3$-$C_6$-cycloalkoxycarbonyl, and, if more than one radical $R^3$ are present, these may be the same or different,
X denotes NH, O or S,
m is equal to 1 or 2, and
n is an integer from 1 to 5,
with the exception of the compounds for which the meanings of the variables are as follows: $R^1$=hydrogen, $R^2$=cyano or ethoxycarbonyl, $R^3$=hydrogen, p-methoxy, m-methyl, or m-chloro, and X=NH.

The invention particularly relates to those aminovinyl-substituted heterocyclic compounds I in which X denotes NH.

The manufacture of the compounds of formula I may be carried out by any of the conventional methods. However, a particularly advantageous method comprises the reaction of a heterocyclic derivative of the general formula II

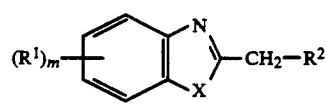

with an aromatic amine of the general formula III

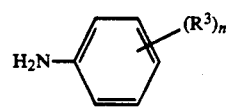

and with a trialkyl orthoformate.

Examples of suitable heterocyclic derivatives II are benzimidazole-2-acetonitrile, methyl benzimidazole-2-acetate, and ethyl benzimidazole-2-acetate, and the corresponding benzoxazole derivatives and benzthiazole derivatives.

Suitable trialkyl orthoformates are trimethyl orthoformate and, in particular, triethyl orthoformate.

The reaction is advantageously carried out in a suitable polar organic solvent, for example an alcohol such as n-propanol, n-butanol, ethylene glycol, diethylene glycol, ethylene glycol monomethyl ether, cyclohexanol, or similar compounds. Other suitable solvents are carboxamides such as dimethyl formate or excess trialkyl orthoformate. In cases where the starting compounds used intrinsically form a liquid mixture, there is no need to add a solvent.

The reaction is normally carried out at a temperature of from 70° to 180° C. and preferably from 100° to 150° C., under atmospheric pressure. The three reactants are advantageously used in equimolar or substantially equimolar proportions, presuming that the trialkyl formate has no additional solvent function. A small excess or one or other of the reactants of, say, up to 15% is acceptable.

If the reaction time for a given combination of reactants is excessively long, it may be desirable to catalyze the reaction by the use of Lewis acids such as $AlCl_3$, $ZrCl_4$, $TiCl_4$, and especially $ZnCl_2$, in conventional amounts.

The recommended method of manufacturing aminovinyl-substituted heterocyclic compounds I containing cycloalkyl radicals or relatively long-chain alkyl radicals in the alkoxycarbonyl groups designated by $R^2$ is to start from a compound I which has short-chain alkoxycarbonyl group(s) $R^2$, for example a methoxycarbonyl derivative or ethoxycarbonyl derivative, and effecting transesterification thereof with an appropriate cycloalkanol or long-chain alkanol in conventional manner.

The aminovinyl-substituted heterocyclic compounds I to be used in the present invention are extremely well suited for stabilizing organic materials to the action of light, oxygen, and heat. They also function as metal deactivators. They are added to the organic materials requiring stabilization in a concentration of from 0.01 to 5% w/w and preferably from 0.02% to 2% w/w, based on the organic material.

By 'organic materials' we mean, for example, cosmetic preparations such as ointments and lotions, medicinal formulations such as pills and suppositories, and precursors of plastics and paint formulations, but mainly the finished plastics and paint formulations themselves.

The present invention further relates to organic material, particularly a plastics or paint formulation, which is stabilized to the action of light, oxygen, and heat, and which contains a compound I in the concentration defined above.

Blending of the compound I to be used in accordance with the present invention with, in particular, plastics formulations may be carried out using any conventional method and equipment for mixing stabilizers or other additives into polymers.

The organic material stabilized with compounds I used in accordance with the present invention may optionally contain other additives, for example anti-oxidants, light stabilizers, metal deactivators, antistatic agents, flame-proofing agents, pigments, and fillers.

Examples of antioxidants and light stabilizers which may be added in addition to the compounds proposed by the invention are compounds based on sterically hindered phenols or co-stabilizers containing sulfur or phosphorus.

Examples of such phenolic antioxidants are 2,6-di-t-butyl-4-methylphenol, n-octadecyl-β-(3,5-di-t-butyl-4-hydroxyphenyl) propionate, 1,1,3-tris(2-methyl-4-hydroxy-5-t-butylphenyl)-butane, 1,3,5-trimethyl-2,4,6-tris-(3,5-di-t-butyl-4-hydroxybenzyl)-benzene, 1,3,5-tris(3,5-di-t-butyl-4-hydroxybenzyl) isocyanurate, 1,3,5-tris[β-(3,5-di-t-butyl-4-hydroxyphenyl)propionylethyl] isocyanurate, 1,3,5-tris(2,6-dimethyl-3-hydroxy-4-t-butylbenzyl) isocyanurate, and pentaerythritol tetrakis[β-(3,5-di-t-butyl-4-hydroxyphenyl)-propionate].

Examples of suitable antioxidants containing phosphorus are tris(nonylphenyl) phosphite, distearyipentaerythritol diphosphite, tris(2,4-di-t-butylphenyl) phosphite, tris(2-t-butyl-4-methylphenyl) phosphite, bis(2,4-di-t-butylphenyl) pentaerythritol diphosphite, and tetrakis(2,4-di-t-butylphenyl)-4,4'-biphenylene diphosphite.

Examples of antioxidants containing sulfur are dilauryl thiodipropionate, dimyristyl thiodipropionate, disrearyl thiodipropionate, pentaerythritol tetrakis(β-lauryl-thiopropionate), and pentaerythritol tetrakis(β-hexyl-thiopropionate).

Other antioxidants and light stabilizers which may be used in conjunction with the compounds I are, for example, 2-(2'-hydroxyphenyl)benztriazoles, 2-hydroxybenzophenones, aryl esters of hydroxybenzoic acids, α-cyanocinammic derivatives, benzimidazole-carboxylic anilides, nickel compounds, and oxalic dianilides.

Particularly good stabilization is achieved by adding at least one light stabilizer to the compound of the general formula I. This stabilizer is selected from the class of compounds comprising the sterically hindered amines and is added in the usual concentrations.

Suitable sterically hindered amines are, for example, bis(2,2,6,6-tetramethylpiperidyl) sebacate, bis(1,2,2,6,6-pentamethylpiperidyl) sebacate, the condensation polymer of 1-hydroxyethyl-2,2,6,6-tetramethyl-4-hydroxypiperidine and succinic acid, the condensation polymer of N,N'-(2,2,6,6-tetramethylpiperidyl)hexamethylene diamine and 4-tert-octylamino-2,6-dichloro-1,3,5-s-triazine, tris(2,2,6,6-tetramethylpiperidyl) nitrilotriacetate, tetrakis(2,2,6,6-tetramethyl-4-piperidyl)-1,2,3,4-butanetetracarboxylic acid, 1,1'-(1,2-ethanedioyl)-bis(3,3,5,5-tetramethylpiperazinone), and the condensation polymers of 4-amino-2,2,6,6-tetramethylpiperidines and tetramethylolacetylene diureas.

Examples of plastics materials which can be stabilized by the compounds I used in accordance with the present invention are as follows:

polymers of monoolefins and diolefins, such as low-density or high-density polyethylenes, polypropylenes, linear polybutene-1, polyisoprene, polybutadiene, and copolymers of monoolefins or diolefins or mixtures of the above polymers;

copolymers of monoolefins or diolefins with other vinyl monomers, for example ethylene/alkyl acrylate copolymers, ethylene/alkyl methacrylate copolymers, ethylene/vinyl acetate copolymers, and ethylene/acrylic acid copolymers;

polystyrene;

copolymers of styrene or α-methylstyrene with dienes and/or acrylic derivatives, for example styrene/butadiene, styrene/acrylonitrile (SAN), styrene/ethyl methacrylate, styrene/butadiene/ethyl acrylate, styrene/acrylonitrile/methyl acrylate, acrylonitrile/butadiene/styrene (ABS), and methyl methacrylate/butadiene/styrene (MBS);

halogen-containing polymers such as polyvinyl chloride, polyvinyl fluoride, polyvinylidene chloride, and copolymers thereof;

polymers derived from α,β-unsaturated acids and their derivatives, for example polyacrylates, polymethacrylates, polyacrylamides, and polyacrylonitriles;

polymers derived from unsaturated alcohols and amines or from their acrylic derivatives or acetals, for example polyvinyl alcohol and polyvinyl acetate;

polyurethanes, polyamides, polyureas, polyesters, polycarbonates, polysulfones, polyethersulfones, and polyetherketones.

The compounds I to be used in accordance with the present invention may also be employed for the stabilization of coats of paint, for example industrially applied coats of paint. Of these, stove-enamel finishes are of particular interest, especially those applied to vehicles, preferably coat-on-coat.

The compounds I may be added to the paint in solid or dissolved form, and their ready solubility in paint formulations is particularly advantageous.

When the compounds I are used in accordance with the present invention as stabilizers for paints, it is also possible to incorporate the aforementioned other additives, especially antioxidants and light stabilizers.

The compounds I to be used in accordance with the present invention are particularly well suited for the stabilization of polystyrene, copolymers of styrene and acrylonitrile (SAN) and of acrylonitrile, butadiene and styrene (ABS), polyurethanes, polyamides, polyolefins, and paints.

A particularly high degree of stabilization of polyurethanes is achieved by adding thereto a mixture of at least one compound of the general formula I, at least one of the aforementioned antioxidants, and at least one of the said sterically hindered amine compounds.

The aminovinyl-substituted heterocyclic compounds I to be used in accordance with the present invention are also effective as light stabilizers in cosmetic preparations, that is, in particular, as a means for protecting the human skin from the harmful effects of light, especially sunlight but also artificial light containing a high proportion of ultraviolet radiation. Thus 'organic material' in its broadest sense includes the human skin. Of course, the cosmetic preparations are themselves stabilized to ensure effectiveness over a maximum period.

Accordingly, the invention further relates to cosmetic preparations containing, as light stabilizer, from 0.1% to 10% w/w and preferably from 1% to 7% w/w, based on the weight of the cosmetic preparation, of one or more aminovinyl-substituted heterocyclic compounds I. Cosmetic preparations of this kind take the form of, for example, liquid, solid, or pasty sun-filter formulations such as creams, lotions, aerosol foams, gels, oils, lipsticks, powders, or sprays.

The compounds I are used in said cosmetic preparations in conventional carriers or diluants, for example as a solution in a cosmetic oil. Commonly used oily constituents of cosmetic preparations are, for example, paraffin oil, glyceryl stearate, isopropyl myristate, diisopropyl adipate, cetylstearyl 2-ethylhexanoate, hydrogenated polyisobutene, petroleum jelly, caprylic/capric triglycerides, microcrystalline wax, lanolin, and stearic acid. One important advantage of the compounds I is that they exhibit good solubility in such oily components.

The compounds I are distinguished by the fact that they are particularly good absorbers of uv-a radiation and show high photostability. They may also be used to advantage in combination with substances conventionally used as uv-b filters, such as the following:
2-hydroxy-4-methoxybenzophenone
2-hydroxy-4-methoxybenzophenone-5-sulfonic acid
ethyl p-aminobenzoate reacted with 25 moles of ethylene oxide
2-ethylhexyl p-methoxycinnamate
2-ethylhexyl p-(N,N-dimethylamino)benzoate
2-phenylbenzimidazole-2-sulfonic acid
3-(4-methylbenzylidene)camphor
2,4,6-trianilino-p-(carbo-2'-ethylhexyl-1'-oxy)-1,3,5-triazine These may be included in the usual amounts and may even cause an increase in the light-stabilizing action due to synergistic factors.

Of particular value for use as light-protecting agents in cosmetic preparations are those aminovinyl-substituted heterocyclic compounds I in which the radical $R^2$ is an alkoxycarbonyl group containing long-chain alkyl. Of particular advantage are straight-chain or, less so, branched-chain $C_6-C_{20}$-alkyl radicals, especially $C_8-C_{18}$-alkyl radicals.

The compounds I to be used in accordance with the present invention are characterized by good compatability with conventional plastics materials and ready solubility in conventional paints and in conventional cosmetic oils. They do not, as a rule, exhibit more than very slight intrinsic color, if at all, and they are stable and non-volatile at the temperatures normally used for processing plastics and paints. Of particular importance is their ability to provide long-term protection of the organic material treated therewith.

MANUFACTURING EXAMPLES

Example 1

23.6 g (0.15 mole) of benzimidazole-2-acetonitrile, 17.6 g (0.16 mole) of p-toluidine, and 25.2g (0.17 mole) of triethyl orthoformate were heated in 60 ml of ethylene glycol over 2 hours to 110° C. Ethanol distilled off slowly and the temperature rose to about 150° C. After the mixture had cooled to 80° C., 120 ml of methanol were added and the whole was allowed to cool to room temperature. The precipitate was removed by filtration and washed with methanol, after which it was recrystallized from n-butanol in the presence of animal charcoal and fuller's earth. 28.6 g of product (corresponding to a yield of 70%) were isolated in the form of pale yellow crystals melting at 247°-248° C.

| | Analysis results: | | |
|---|---|---|---|
| | C | H | N |
| calculated: | 74.43 | 5.14 | 20.42 |
| found: | 74.0 | 5.3 | 20.5 |

The spectroscopic data are listed in Table 1 below.

Example 2

24.5 g (0.12 mole) of ethyl benzimidazole-2-acetate, 11.6 g (0.125 mole) of aniline, and 19.6 g (0.132 mole) of triethyl orthoformate were heated in 90 ml of ethylene glycol to 100° C., after which the ethanol formed during the reaction was distilled off over a period of from 1 to 2 hours, during which time the temperature rose to about 140° C. After the mixture had cooled to 70° C., 100 ml of ethanol were added, and the mixture was then cooled to room temperature and filtered to isolate the precipitate which had formed. The yellowish brown crude product was recrystallized from ethanol in admixture with animal charcoal. 26.3 g of product (corresponding to a yield of 71.5%), were isolated in the form of colorless crystals, m.p. 162°-163° C.

| | Analysis results: | | | |
|---|---|---|---|---|
| | C | H | N | O |
| calculated: | 70.36 | 5.54 | 13.68 | 10.6 |
| found: | 70.40 | 5.6 | 13.6 | 10.4 |

The spectroscopic data are listed in Table 1 below.

Examples 3 to 22

Following the procedures described in Example 1 and Example 2, appropriate aromatic amines III were used to prepare the products listed in Table 1 below from benzimidazole-2-acetonitrile (cf. Example 1 ) or ethyl benzimidazole-2-acetate (cf. Example 2) and triethyl orthoformate. The melting points and spectroscopic data of the products are again listed in Table 1.

Example 23

8.0 g (0.026 mole) of the compound obtained in Example 2 were suspended in 40 g (0.25 mole) of isodecanol in admixture with 1 g of $Na_2CO_3$, and the mixture was heated at a temperature of from 140° to 145° C. for 19 hours while nitrogen was bubbled through. The hot mixture was filtered to remove the inorganic salt, and the alcohol was distilled off from the filtrate in vacuo. The residue was triturated with methanol and isolated by filtration. There were obtained 8.1 g of product (corresponding to a yield of 74.3 %) in the form of colorless crystals melting at 80°-83° C.

| Analysis results: | | | | |
|---|---|---|---|---|
| | C | H | N | O |
| calculated: | 74.43 | 7.93 | 10.02 | 7.73 |
| found: | 74.1 | 7.9 | 10.0 | 8.2 |

The spectroscopic data are listed in Table 1 below.

Examples 24 to 26

Following the procedure described in Example 23, the products obtained in Examples 14, 18, and 22 were used together with an appropriate long-chain alcohol, i.e. isodecanol or 2-ethylhexanol, to produce the compounds listed in Table 1 below. The melting points and the spectroscopic data of these compounds are also listed in said Table.

Example 27

A mixture of 24.6 g (0.12 mole) of ethyl benzoxazole-2-acetate, 11.6 g (0.125 mole) of aniline, 19.6 g (0.132 mole) of triethyl orthoformate, and 0.5 g of zinc chloride was heated to 100° C. The ethanol formed during the reaction was distilled off over a period of 1 hour, during which time the temperature rose to about 120° C. 100 ml of ligroin (boiling range 70°-80° C.) were then added at 70° C., and the mixture was cooled to room temperature, after which the resulting precipitate was isolated by filtration. The crude product thus obtained was recrystallized from ethanol in admixture with animal charcoal. The product was obtained in the form of colorless crystals melting at 95°-96° C., in a yield of 88%.

The spectroscopic data are contained in Table 1 below.

Examples 28 to 32

The manufacturing procedure used in Examples 28, 29, 31, and 32 is similar to that described in Example 27. Example 30 involved treatment of the product from Example 29 in a manner similar to that described in Example 23, using 2-ethylhexanol. The structures, melting points and spectroscopic data of the products are listed in Table 1.

TABLE 1

Structure, Melting Point and Spectroscopic Data of Aminovinyl-Substituted Heterocyclic Compounds I Produced in the Examples

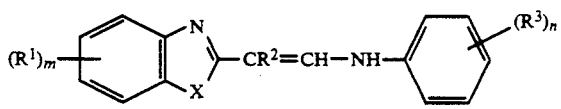

I

| Ex. No. | Structure | | | M.P. [°C.] | UV Data (CH$_3$OH) | |
|---|---|---|---|---|---|---|
| | $R^2$ | $R^3$ | n | | $\lambda$max [nm] | $\epsilon$ |
| X = NH (benzimidazoles) | | | | | | |
| 1. | CN | 4-CH$_3$ | 1 | 247–248 | 359 | 35300 |
| 2. | COOC$_2$H$_5$ | H | 1 | 162–163 | 355 | 39500 |
| 3. | CN | 4-OC$_2$H$_5$ | 1 | 225 | 360 | 34300 |
| 4. | CN | 4-COOC$_2$H$_5$ | 1 | 258 | 367 | 48600 |
| 5. | CN | 2-OCH$_3$ 5-Cl | 2 | 260 | 368 | 33600 |
| 6. | CN | 3-CH$_3$ 4-CH$_3$ | 2 | 251 | 359 | 38300 |
| 7. | CN | 3-CH$_3$ 5-CH$_3$ | 2 | 269–271 | 359 | 35500 |
| 8. | CN | 2-CH$_3$ 6-CH$_3$ | 2 | 273 | 331 | 30000 |
| 9. | CN | 2-COOCH$_3$ | 1 | 225 | 365 | 27300 |
| 10. | CN | 2-CH$_3$ | 1 | 248 | 360 | 34700 |
| 11. | CN | 3-CH$_3$ | 1 | 228 | 357 | 35300 |
| 12. | CN | 4-CN | 1 | 313 | 366 | 28500 |
| 13. | CN | 2-CH$_3$ 4-OCH$_3$ | 2 | 204–206 | 362 | 32000 |
| 14. | COOC$_2$H$_5$ | 4-CH$_3$ | 1 | 201 | 358 | 21700 |
| 15. | COOC$_2$H$_5$ | 2-CH$_3$ | 1 | 148 | 359 | 34300 |
| 16. | COOC$_2$H$_5$ | 4-OC$_2$H$_5$ | 1 | 180–182 | 360 | 32500 |
| 17. | COOC$_2$H$_5$ | 3-CH$_3$ | 1 | 147 | 356 | 31900 |
| 18. | COOC$_2$H$_5$ | 4-COOC$_2$H$_5$ | 1 | 183 | 369 | 43500 |
| 19. | COOC$_2$H$_5$ | 3-CH$_3$ 5-CH$_3$ | 2 | 172 | 362 | 36500 |
| 20. | COOC$_2$H$_5$ | 3-CH$_3$ 4-CH$_3$ | 2 | 171 | 358 | 35200 |
| 21. | COOC$_2$H$_5$ | 3-OCH$_3$ 4-OCH$_3$ | 2 | 162 | 372 | 32600 |
| 22. | COOC$_2$H$_5$ | 2-CH$_3$ 4-OCH$_3$ | 2 | 206 | 363 | 30000 |
| 23. | COO-iso-C$_{10}$H$_{21}$ | H | 1 | 80–83 | 356 | 33600 |
| 24. | COO-iso-C$_{10}$H$_{21}$ | 4-CH$_3$ | 1 | 80–82 | 358 | 32100 |
| 25. | COO-C$_8$H$_{17}$ | 4-COO—C$_8$H$_{17}$ | 1 | 60 | 370 | 48900 |
| 26. | COO-C$_8$H$_{17}$ | 2-CH$_3$ 4-OCH$_3$ | 2 | 76–78 | 362 | 33000 |
| X = O (benzoxazoles) | | | | | | |
| 27. | COOC$_2$H$_5$ | H | 1 | 95–96 | 351 | 32500 |
| 28. | COOC$_2$H$_5$ | 4-OCH$_3$ | 1 | 95–96 | 355 | 31600 |
| 29. | COOC$_2$H$_5$ | 4-COOC$_2$H$_5$ | 1 | 134–36 | 363 | 44000 |

TABLE 1-continued

Structure, Melting Point and Spectroscopic Data of Aminovinyl-Substituted Heterocyclic Compounds I Produced in the Examples

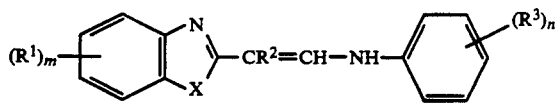

I

| Ex. No. | Structure $R^2$ | $R^3$ | n | M.P. [°C] | UV Data ($CH_3OH$) $\lambda max$ [nm] | $\epsilon$ |
|---|---|---|---|---|---|---|
| 30. | $COOC-C_8H_{17}$ | $4\text{-}COO-C_8H_{17}$ | 1 | oily | 363 | 41600 |
| 31. | $COOC_2H_5$ | $4\text{-}CH_3$ | 1 | 123 | 353 | 30800 |
| 32. | $COOC_2H_5$ | $4\text{-}COO-C_8H_{17}$ | 1 | 63–65 | 363 | 42600 |

Remarks

The following is valid for all Examples: $R^1=H$; $m=1$. In Examples 25, 26, 30, and 32, $C_8H_{17}$ designates a 2-ethylhexyl radical. In Examples 25 and 30 transesterification additionally occurred at the 4-$COOC_2H_5$ group on the phenyl nucleus.

Examples of Application

Polyurethane specimens for exposure tests were prepared as follows:

To a mixture of
100 g of a polyol component having the following composition:
 41.9 g of a polyetherol having an OH number of 29 and containing about 84% of primary hydroxyl groups and obtained by the addition of propylene oxide and ethylene oxide to polypropylene glycol,
 42.5 g of a polyetherol having an OH number of 27 and containing about 88% of primary hydroxyl groups and obtained by the addition of propylene oxide and ethylene oxide to trimethylol propane, and
 8.1 g of butane-1,4-diol
1.7 g of a 25% w/w solution of 1,4-diazabicyclo[2.2.2]octane in butane-1,4-diol,
0.02 g of dibutyltin laurate,
0.1 g of a conventional silicone stabilizer
5.5 g of fluorotrichloromethane, and
0.2 g of water
there were added
0.5 g of the product obtained in Example 2 or, for comparison, the same amount of a prior art agent,
0.5 g of bis(1,2,2,6,6-pentamethylpiperidyl) sebacate, and
25 g of an antioxidant mixture comprising 9% w/w of α-tocopherol and 91% w/w of tris(nonylphenyl) phosphite,
and the resulting mixture was foamed to test specimens using
 48.5 g of a prepolymer containing 23% w/w of isocyanate groups and prepared from
 87.2% w/w of 4,4'-diphenylmethane diisocyanate,
 4.8% w/w of a polyetherol having an OH number of 250 and obtained by the addition of propylene oxide to propylene glycol, and
 8.0% w/w of dipropylene glycol
at a mold and material temperature of 25° C.

The specimens were subjected to exposure tests using a Hanau Xenotest ®450, and the degree of discoloration was determined by measuring the Yellowness Index (YI) as specified in the *Annual Book of ASTM Standards D* 1925-70 (Reapproved 1977). The results are listed in Table 2 below.

TABLE 2

Yellowness Indices of Polyurethane Specimens

| | following exposure for | |
|---|---|---|
| | 48 h | 96 h |
| Invention: | | |
| Substance obtained in Ex. 2 | 11.5 | 14.0 |
| Substance obtained in Ex. 23 | 12.4 | 13.4 |
| Comparison: | | |
| No stabilizer | 41.4 | 53.1 |
| Prior art stabilizer* | 13.1 | 15.8 |

*compound of the formula

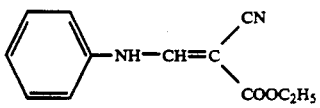

as proposed in US-A 3,079,366 (1).

Tests in application technology to determine the suitability of the products for cosmetic applications encompassed solubility tests and tests on the photostability of samples in cosmetic oils.

Solubility Tests

The solubilities of the products of Examples 25 and 30 in paraffin oil, cetylstearyl 2-ethylhexanoate, caprylic/capric triglycerides and $C_{12}$–$C_{15}$-alcohol benzoates were found to be better than 10% w/w.

Photostability

Measurements of the photostability were carried out in a solvent mixture of $C_{12}$–$C_{15}$-alcohol benzoates. The compounds listed in Table 3 below were dissolved therein to form separate solutions having a concentration of 10 mg/liter, which were then irradiated with a xenon lamp. The degree of degradation was taken to be the percentage reduction in extinction of the absorption bands of greatest wavelength after a given period of irradiation. The results are shown in Table 3.

TABLE 3

| Example No. | Extinction after x hours of irradiation | |
|---|---|---|
| | x = 0 | x = 6 |
| 25 | 0.805 (100%) | 0.788 (97.9%) |
| 30 | 0.757 (100%) | 0.719 (95.0%) |

We claim:
1. A process for the stabilization of organic materials, which comprises admixing with said organic materials a stabilizing amount of an aminovinyl-substituted heterocyclic compound of the formula I:

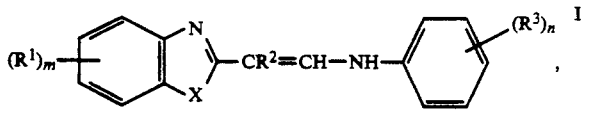

in which
- $R^1$ denotes hydrogen, $C_1$-$C_4$-alkyl, $C_1$-$C_4$-alkoxy, or halogen, and, if more than one radical $R^1$ are present, these may be the same or different,
- $R^2$ denotes cyano or $C_1$-$C_{20}$-alkoxycarbonyl or $C_3$-$C_6$-cycloalkoxycarbonyl,
- $R^3$ denotes hydrogen, $C_1$-$C_{18}$-alkyl, $C_1$-$C_{18}$-alkoxy, halogen, cyano, $C_1$-$C_{20}$-alkoxycarbonyl, or $C_3$-$C_6$-cycloalkoxycarbonyl, and, if more than one radical $R^3$ are present, these may be the same or different,
- X denotes NH, O or S,
- m is equal to 1 or 2, and
- n is an integer from 1 to 5.

2. The process according to claim 1, wherein
- $R^1$ denotes hydrogen, methyl, methoxy, or chlorine,
- $R^2$ denotes cyano or $C_1$-$C_{20}$-alkoxycarbonyl,
- $R^3$ denotes hydrogen, $C_1$-$C_4$-alkyl, $C_1$-$C_4$-alkoxy, chlorine, cyano, or $C_1$-$C_{12}$-alkoxycarbonyl,
- X denotes NH,
- m is equal to 1 or 2, and
- n is equal to 1 or 2.

3. The process according to claim 1, wherein
- $R^1$ denotes hydrogen,
- $R^2$ denotes $C_1$-$C_{20}$-alkoxycarbonyl,
- $R^3$ denotes hydrogen, methyl, ethyl, methoxy, ethoxy, chlorine, cyano, or $C_{1-8}$-alkoxycarbonyl,
- X denotes NH, and
- n is equal to 1 or 2.

4. An organic material stabilized to the action of light, oxygen, and heat and containing from 0.01% to 5% w/w, based on the weight of the organic material, of one or more aminovinyl-substituted heterocyclic compounds I as claimed in claim 1.

5. A plastics material or paint stabilized to the action of light, oxygen, and heat and containing from 0.01% to 5% w/w, based on the weight of the plastics material or paint, of one or more aminovinyl-substituted heterocyclic compounds I as claimed in claim 1.

6. A cosmetic preparation containing, as light stabilizer, from 0.1% to 10% w/w, based on the weight of the cosmetic preparation, of one or more aminovinyl-substituted heterocyclic compounds I as claimed in claim 1.

7. The process according to claim 1, wherein said organic material is a plastic material or paint.

8. A method of protecting human skin from the action of light, comprising applying to said skin an effective amount of a cosmetic preparation comprising from 0.1 to 10% w/w, based on the weight of said cosmetic preparation, of one or more compounds of the formula I:

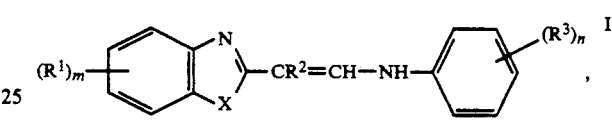

which
- $R^1$ denotes hydrogen, $C_1$-$C_4$-alkyl, $C_1$-$C_4$-alkoxy, or halogen, and, if more than one radical $R^1$ are present, these may be the same or different.
- $R^2$ denotes cyano or $C_1$-$C_{20}$-alkoxycarbonyl or $C_3$-$C_6$-cycloalkoxycarbonyl,
- $R^3$ denotes hydrogen, $C_1$-$C_{18}$-alkyl, $C_1$-$C_{18}$-alkoxy, halogen, cyano, $C_1$-$C_{20}$-alkoxycarbonyl, or $C_3$-$C_6$-cycloalkoxycarbonyl, and, if more than one radical $R^3$ are present, these may be the same or different.
- X denotes NH, O or S,
- m is equal to 1 or 2, and
- n is an integer from 1 to 5.

* * * * *